(12) United States Patent
Chin et al.

(10) Patent No.: US 8,026,071 B2
(45) Date of Patent: Sep. 27, 2011

(54) SYSTEMS AND METHODS FOR DETECTING TARGET ANALYTES

(75) Inventors: Robert C Chin, Austin, TX (US); Gregory F. Lopreato, Austin, TX (US)

(73) Assignee: Fabrico Technology, Inc., Austin, TX (US)

( * ) Notice: Subject to any disclaimer, the term of this patent is extended or adjusted under 35 U.S.C. 154(b) by 504 days.

(21) Appl. No.: 12/046,964

(22) Filed: Mar. 12, 2008

(65) Prior Publication Data

US 2008/0311677 A1    Dec. 18, 2008

Related U.S. Application Data

(60) Provisional application No. 60/894,371, filed on Mar. 12, 2007.

(51) Int. Cl.
*G01N 33/53* (2006.01)

(52) U.S. Cl. .......................... 435/7.1; 435/7.2

(58) Field of Classification Search .................. None
See application file for complete search history.

(56) References Cited

U.S. PATENT DOCUMENTS

| | | | |
|---|---|---|---|
| 4,916,081 A | | 4/1990 | Kamada et al. |
| 5,055,408 A | | 10/1991 | Higo et al. |
| 5,123,901 A | * | 6/1992 | Carew .......................... 604/5.02 |
| 5,374,395 A | | 12/1994 | Robinson et al. |
| 5,567,588 A | | 10/1996 | Gold et al. |
| 5,698,450 A | | 12/1997 | Ringrose et al. |
| 5,981,297 A | | 11/1999 | Baselt |
| 6,133,043 A | | 10/2000 | Talley et al. |
| 6,582,381 B1 | | 6/2003 | Yehezkeli et al. |
| 6,649,419 B1 | | 11/2003 | Anderson |
| 6,939,677 B1 | | 9/2005 | Ceriani et al. |
| 2001/0008760 A1 | * | 7/2001 | King et al. ........................ 435/5 |
| 2004/0086918 A1 | | 5/2004 | Lowey et al. |

FOREIGN PATENT DOCUMENTS

| | | |
|---|---|---|
| WO | 2004053490 A1 | 6/2004 |
| WO | 2005015216 A1 | 8/2010 |

OTHER PUBLICATIONS

Richardson et al. (Biosensors & Bioelecrtronics 2001 vol. 16, p. 989-993.*

Bowtell, David D. L.; "Options Available—from Start to Finish—for Obtaining Expression Data by Microarray";Nature America Inc.; vol. 21 (Jan. 1999) (8 pages).
Kriz, Christine Berggren, et al; "Magnetic Permeability Measurements in Bioanalysis and Biosensors"; Analytical Chemistry 1996, 68, 1966-1970; (5 pages).
Carulli, John P., et al; "High Throughput Analysis of Differential Gene Expression"; Journal of Cellular Biochemistry Supplements 30/31; 286-296 (1998) (11 pages).
Current Patents Gazette; Thomson, Issue 0520, May 20, 2005, (2 pages).
Drolet, Daniel W., et al; "An Enzyme-Linked Oligonucleotide Assay"; Nature Biotechnology, vol. 14, Aug. 1996; (5 pages).
Enpuku, Keiji, et al; "Detection of Magnetic Nanoparticles with Superconducting Quantum Interference Device (SQUID) Magnetometer and Application to Immunoassays"; Jpn. J. Appl. Phys., vol. 38 (1999) pp. L1102-L1105; (4 pages).
Keller, Walter, et al; "Degradation of DNA RNA Hybrids by Ribonuclease H and DNA Polymerases of Cellular and Viral Origin"; Proc. Nat. Acad. Sci. USA; vol. 69, No. 11, pp. 3360-3364, Nov. 1972 (5 pages).
Kriz, Kirstin, et al; "Advancements Toward Magneto Immunoassays"; El Sevier, Biosensors & Bioelectronics 13 (1998) pp. 817-823 (7 pages).
Luxton, Richard, et al; "Use of External Magnetic Fields to Reduce Reaction Times in an Immunoassay Using Micrometer-Sized Paramagnetic Particles as Labels (Magnetoimmunoassay)"; Analytical Chemistry, vol. 76, No. 6, Mar. 15, 2004 pp. 1715-1719 (5 pages).
Pathak, Rashmi, et al; "Subtractive Differential Display: a Modified Differential Display Technique for Isolating Differentially Expressed Genes"; Molecular Biology Rep. (2007) vol. 34; pp. 41-46 (6 pages).
Richardson, Julie, et al; "A Novel Measuring System for the Determination of Paramagnetic Particle Labels for use in Magneto-Immunoassays"; Elsevier, Biosensors & Bioelectronics 16 (2001) pp. 1127-1132 (6 pages).
Stein, J., et al; "Differential Display Technology: a General Guide"; CMLS Cellular and Molecular Life Sciences, vol. 59 (2002) pp. 1235-1240 (6 pages).

* cited by examiner

*Primary Examiner* — Jacob Cheu
(74) *Attorney, Agent, or Firm* — Larson Newman, LLP

(57) ABSTRACT

A method of detecting a target substance includes contacting the target substance with a substrate. The substrate has a first receptor bound to the substrate. The target substance binds to the first receptor. The method further includes contacting a second receptor with the substrate. The second receptor is associated with the target substance. The second receptor is biotinylated. The method also includes contacting an anti-biotin antibody conjugated paramagnetic particle with the substrate.

20 Claims, 9 Drawing Sheets

SYSTEMS AND METHODS FOR DETECTING TARGET ANALYTES

CROSS-REFERENCE TO RELATED APPLICATION

The present application claims priority from U.S. Provisional Patent Application No. 60/894,371, filed Mar. 12, 2007, entitled "SYSTEM AND METHODS FOR DETECTING TARGET ANALYTES," naming inventors Robert Chin and Gregory F. Lopreato, which application is incorporated by reference herein in its entirety.

GOVERNMENT LICENSE RIGHTS

The U.S. government has a paid-up license in this invention and the right in limited circumstances to require the patent owner to license others on reasonable terms as provided for by the terms of FA8650-06-C-6646 awarded by USAF/AFMC Air Force Research Laboratory.

This invention was made with Government support under FA8650-06-C-6646 awarded by USAF/AFMC Air Force Research Laboratory. The Government has certain rights in the invention.

FIELD OF THE DISCLOSURE

This disclosure, in general, relates to systems and method for detecting target analytes.

BACKGROUND

Increasingly, industry is seeking detection methods for low concentration analytes. From detection of early stages of disease to early warning of chemical and biological hazards, detection of analytes increasing is becoming of concern to society.

In particular, medicine is seeking to detect viral infections, such as HIV, at earlier stages. Early stage detection leads to treatment when a disease in manageable. For example, antiviral medications have shown increased efficacy, possibly to the point of curing infected HIV patients when administered early. In other examples, early detection of avian influenza may lead to improved treatment of patients and prevention of epidemics.

In another example, militaries and civil defense agencies are seeking early warning and detection systems for chemical and biological agents. With increased threat of terrorism and rogue governments, concern about chemical or biological attacks has grown. Detection of analytes and residue relating to such agents may lead to improved security and faster response, ultimately saving lives.

Further, analyte detection is useful in research. Industry is seeking to automate and miniaturize experimentation, leading to a desire for detection methods that are sensitive and may be performed with small quantities. However, traditional methods are often expensive and inefficient. For example, gas chromatography and mass spectrometry use large cumbersome equipment that is expensive to maintain. In other exemplary methods, such as test strips and titration, the output is less sensitive to reagents and analytes. In addition, such methods, while convenient, are inaccurate and often, subjective. For biological samples, culture methods are time consuming and use expert training to achieve results. In particular, DNA testing through gel electrophoresis is time consuming and utilizes a large quantity of DNA. While the DNA may be replicated to produce the quantity used in testing, such replication adds time to the testing process.

As such, an improved method of detecting analytes would be desirable.

BRIEF DESCRIPTION OF THE DRAWINGS

The present disclosure may be better understood, and its numerous features and advantages made apparent to those skilled in the art by referencing the accompanying drawings.

DESCRIPTION OF THE EMBODIMENTS

In a particular embodiment, a method of detecting a target analyte includes contacting the target analyte with a substrate. In an exemplary embodiment, the substrate is a multi-well plate. A first receptor that binds to the target analyte may be bound to the substrate. The method also includes contacting a second receptor, reactive to the target analyte, with the substrate. The second receptor may be conjugated to a paramagnetic particle. Alternatively, the method may include applying a conjugated paramagnetic particle that is reactive with the second receptor to the substrate.

In another embodiment, a detection kit includes a substrate having a first receptor and includes a second receptor. The first receptor and the second receptor may be responsive to a target analyte. For example, the first and second receptors may bind the target analyte. The second receptor may be conjugated to a paramagnetic particle. Alternatively, the detection kit may include a conjugated paramagnetic particle that is responsive to the second receptor. In a particular example, the second receptor may be biotinylated and the conjugated paramagnetic particle may be conjugated with an anti-biotin antibody.

Figure 1:
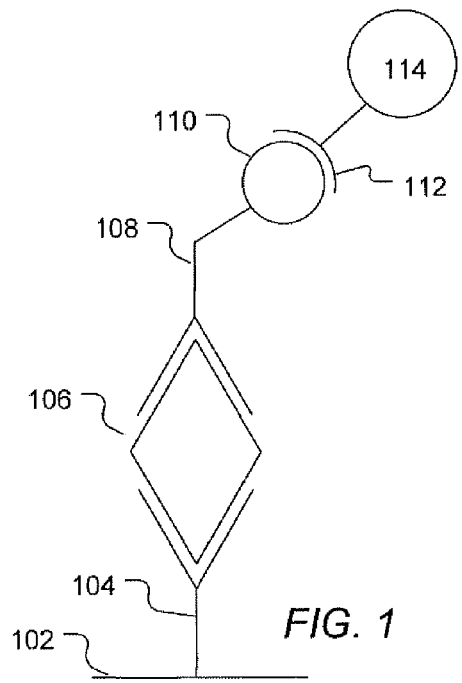
FIGS. 1, 2*a*, 2*b*, and 2*c* include illustrations of exemplary assays to detect target analytes using conjugated paramagnetic particles.

FIG. 1 includes a diagram illustrating an exemplary assay to detect a target analyte 106. In an exemplary embodiment, a substrate 102 includes a receptor 104. For example, the substrate 102 may include a polymeric material or a ceramic material, such as glass. In another example, the substrate 102 includes a semiconductor material. In a further example, the substrate is a well of a multi-well plate.

The receptor 104 may bind the target analyte 106. For example, a portion of the target analyte 106 may bond to a portion of the receptor 104. Further, a receptor 108 may bind to the target analyte 106. For example, a portion of the receptor 108 may bind to a portion of the target analyte 106. In an exemplary embodiment, the receptor 108 includes a characteristic site 110, such as a conjugated biotin or a distal protein chain. A conjugated paramagnetic particle 114 may include a receptor 112 adapted to bind to the characteristic site 110 of the receptor 108. For example, an anti-biotin antibody conjugated to the conjugated paramagnetic particle 114 may bind to a biotin attached to the receptor 108.

In an exemplary embodiment, the amount of the target analyte 106 may be determined from the amount of conjugated paramagnetic particle 114 associated with the substrate. For example, a solution including conjugated paramagnetic particles 114 may be washed over the substrate 102 after the substrate 102 has been exposed to a solution suspected of including the target analyte and after the substrate 102 has been exposed to the receptor 108. After washing and optionally, drying, the number of paramagnetic particles 114 remaining in proximity to the substrate 102 may be correlated with the amount of target analyte 106 in the solution suspected of having the target analyte 106. Such paramagnetic particles 114 may be detected using, for example, a coil or antenna coupled to a detection circuitry.

In an exemplary embodiment, a receptor includes a chemical structure adapted to respond to the target. In a particular example, the receptor includes sites that bind with one or more sites located on the target. In an example, the receptor is non-specific and can bind to more than one type of target. For example, the receptor may bind to many targets of different types. In an example, a non-specific receptor can bind to many proteins of a particular animal or plant species, such as human, any one of the apes, any one of the rodents, or any one of the avian species. Alternatively, the receptor may be specific and can bind to a specific target, exclusive of other targets. For example, the receptor may bind to a specific antigen, such as a particular virus, a particular chemical, or a particular protein.

In a particular embodiment, the receptor may be formed from an antibody, a protein, or a nucleic acid sequence. In an example, the receptor may include an anti-body. For example, a tissue sample or a target substance may be introduced into an animal subject that forms antibodies to aspects of the tissue sample or the target substance. Such antibodies may be isolated and prepared for use as receptors. An antibody may bind specifically to a particular virus, a particular metabolite, a particular protein, a particular drug, or a particular chemical or biological warfare agent. In an alternative example, the receptor may be an antigen useful in detecting an antibody.

Depending on the nature of the target analyte, an animal system may be selected to enhance the detection method. For example, the target analyte may be injected into a selected animal system to develop a receptor, such as an antibody. Based on the selected animal system, a paramagnetic particle may be conjugated to an antibody selective for the proteins of the selected species of animal. For example, the animal system may be selected from an avian species, such as a goose, a chicken, a duck, a swan, or a wild bird species. In another example, the animal system may be selected from a greater ape species, such as an orangutan, a gibbon, a siamang, a gorilla, a chimpanzee, or a bonobo, or from a monkey, such as a rhesus, a macaque, a baboon, a vervet, a squirrel monkey, an owl monkey, a tamarin, or a marmoset. In a further example, the antibody may be a human antibody. In a particular embodiment, the antibody may be formed in a traditional system, such as a rodent, rabbit, goat, or horse. As such, the paramagnetic particle may be conjugated to a corresponding antibody responsive to proteins of the selected animal species, such as an anti-orangutan, an anti-chimpanzee, an anti-tamarin, an anti-chicken, or an anti-goose antibody. In an alternative embodiment, the receptor is biotinylated and the paramagnetic particle is conjugated to an anti-biotin receptor. An exemplary anti-biotin receptor includes avidin or streptavidin. Alternatively, the anti-biotin receptor may be an anti-biotin antibody, which may have particular advantage in more specific binding to biotinylated antibody type receptors.

In another example, the receptor may be a nucleic acid sequence, such as a DNA or an RNA sequence. In a particular example, the nucleic acid sequence forms a strand of oligonucleotides, often referred to as an aptamer, that can bind to a specific target. In an embodiment, an aptamer may be selected that binds to a specific target, such as a chemical species. For example, an aptamer may be selected that binds to a chemical or biological warfare agent. In another example, an aptamer may be selected to bind to residues of drugs and explosives. In particular, aptamers may be small and may be particularly suited to bind to small molecules. In a further example, an aptamer may be selected to bind to a particular sequence of DNA or RNA.

In an exemplary embodiment, the receptors may be bonded or coupled to the surface of the substrate. In another example, the receptors may be conjugated to a paramagnetic particle. In a further example, the receptor may be biotinylated or may be used as a layer of a multi-layer detection protocol.

A conjugated paramagnetic particle is a particle formed of a paramagnetic material on the surface of which a conjugated molecule is bound. The conjugated molecule may be reactive to bind with particular molecules, such as proteins, nucleic acid sequences, or small molecule chemicals.

The target is generally an analyte to be detected. For example, the target may be an in vivo endogenous target derived from a tissue or fluid sample of a species and in particular, may be an antigen. In an example, the endogenous target may be derived from a fluid, such as blood, plasma, serum, urine, sweat, tears, saliva, ejaculate, or from a tissue, bone, or hair. The endogenous target, for example, may be a protein, such as a protein expressed by a subject. A particular example includes a prion. In a further example, the endogenous target may be a metabolite indicative of a disease. In an additional example, the endogenous target may be toxic metabolite derived from a biological source. In a further example, the endogenous target may include a sequence of DNA or RNA. Alternatively, the target may be an in vivo exogenous target, such as a virus or bacteria. An exemplary exogenous target may include a virus, such as a human immunodeficiency virus (HIV), an influenza virus such as H5N1, a cold virus, or a hepatitis virus. In another example, the exogenous target may include a biological warfare agent when derived from bodily fluid or tissue. Such a biological warfare agent may include anthrax, brucellosis, cholera, Congo-Crimean hemorrhagic fever, Ebola hemorrhagic fever, melioidosis, plague, Q-fever, rift valley fever, smallpox, tularemia, Venezuelan equine encephalitis, ricin, saxitoxin, staphylococcal enterotoxin B, clostribium perfringens toxin, botulinum toxin, or trichothecene mycotoxin.

Alternatively, the target may be an ex vivo target and may be derived from an environmental source. For example, the target may be derived from water, such as water derived from an ocean, sea, lake or tributary, rainwater, dew, or potable water supplies. In another example, the exogenous target may be derived from air, soil, or rock.

In a particular embodiment, an ex vivo target may include a drug, a chemical warfare agent, an explosive, or a residue thereof. An exemplary drug may include cocaine, methamphetamine, heroin, marijuana, or LSD. An exemplary warfare agent may include Somin, Sarin, VX, Tabu, nerve gas, or any combination thereof. An exemplary explosive may include TNT, thermite, thermate, nitroglycerin, gun powder, Semtex, RDX, PETN, HMX, TETRYL, AMATOL, ANFO, COMP A-3, COMP B-3, COMP C-4, or any combination thereof. For example, an exemplary explosive residue target may include acetic anhydride, acetone, alcohol, ammonia, ammonium nitrate, aniline, azides, camphor, coal tar, diatomaceous earth, diazo compounds, fulminates, glycerol, guano, guncotton, nitric acid, nitroglycerin, phenol, potassium nitrate, saltpeter, transuranium elements, urea, or any combination thereof.

Figure 2A:
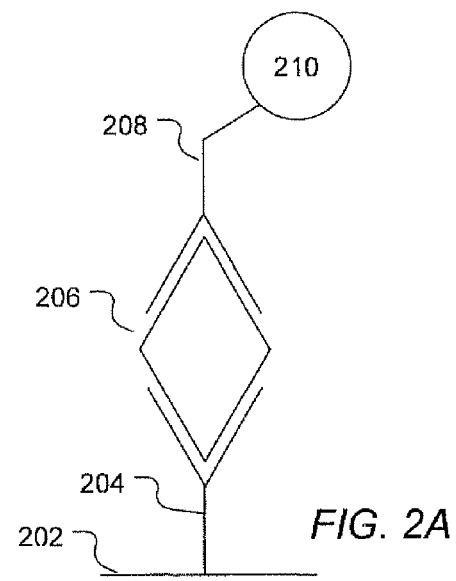

As illustrated in FIG. 1, the target analyte may be bound between two receptors and a conjugated paramagnetic particle, may bind to a distal end of one of the receptors. Alternatively, the target analyte may be bound to a receptor included on the substrate and a conjugated paramagnetic particle may bind to the target analyte. FIG. 2a includes a diagram illustrating an exemplary assay to detect a target analyte 206. In the exemplary embodiment, a substrate 202 is attached to a receptor 204. The receptor 204 may bind the target analyte 206. Further, a receptor 208 may bind the target analyte 206. In an exemplary embodiment, the receptor 208 is conjugated to a paramagnetic particle 210. In an example, the amount of the target analyte 206 may be determined from the number of conjugated paramagnetic particles 210 associated with the substrate.

Figure 2B:
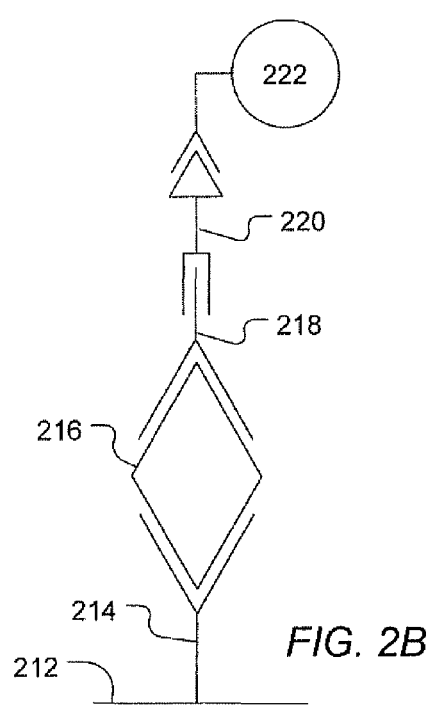

In alternative embodiments, multiple layers of receptors may be used to bind the conjugated paramagnetic particle to the target analyte. For example, FIG. 2b includes an illustration of a substrate 212 including a receptor 214. The receptor 214 may bind to a target analyte 216. A second receptor 218 may bind to the target analyte 216. In addition, a third receptor 220 may bind to a site on the second receptor 218 and a receptor conjugated to the paramagnetic particle 222 may bind to the third receptor 220.

Figure 2C:
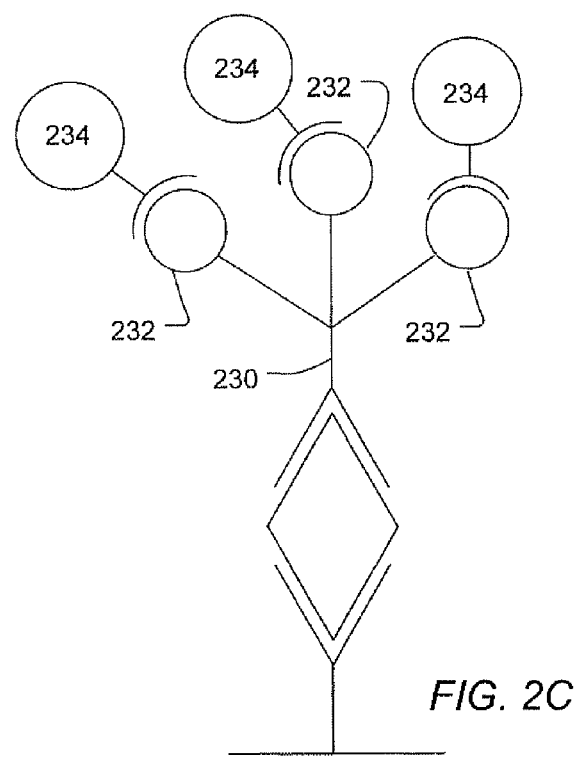

In a further example, the receptor may include more than one characteristic site to which a further receptor or conjugated paramagnetic particle may bind. For example, the receptor may be biotinylated with more than one biotin molecule and more than one anti-biotin conjugated paramagnetic particle may bind to the receptor. For example, FIG. 2c includes an illustration of a receptor 230 including more than one characteristic site 232 bonded to a conjugated paramagnetic particle 234.

In a particular embodiment, a substrate may include a receptor, such as a bound antibody (specific or non-specific), an aptamer, biotin, streptavidin, an active protein, or any combination thereof. The receptor is responsive to an intended target analyte. In an example, a specific anti-body may be a second receptor. The specific antibody may be conjugated to a paramagnetic particle or may include characteristic groups to which surface groups of the conjugated paramagnetic particle can bind.

In another example, the second receptor (not bound to the substrate) can be a non-specific antibody. For example, when the target analyte is endogenous to a particular species, the non-specific analyte may bind to more than one type of endogenous analytes from that species. The second receptor can be conjugated directly to a conjugated paramagnetic particle. Alternatively, the second receptor can include characteristic groups to which a conjugated paramagnetic particle can bind. In a further example, a specific second receptor derived from a particular species can be used to bind a target analyte and a non-specific anti-body active to the particular species can be conjugated to a conjugated paramagnetic particle.

In a further exemplary embodiment, the first receptor (bound to a substrate) or the second receptor (not bound to the substrate) can be an aptamer. For example, an aptamer receptor can be advantageous for use in binding small molecule chemical target analytes or nucleic acid sequence target analytes. In a particular example, an aptamer can be used as a second receptor that is conjugated to a paramagnetic particle. In general, when an aptamer is used as a receptor, it may be advantageous to use an aptamer for both the first and second receptors.

In another exemplary embodiment, the second receptor can be conjugated to a streptavidin group. As such, a conjugated paramagnetic particle that is responsive to the streptavidin group can be used to bind to the second receptor. In an example, the conjugated paramagnetic particle may be biotinylated. In another example, the conjugated paramagnetic particle may be conjugated to an anti-streptavidin antibody.

In an additional example, the first receptor can be bound to the substrate using a streptavidin-biotin system. For example, biotin can be bound to the substrate and a receptor conjugated to streptavidin may be used to bind the biotin. In another example, streptavidin may be bound to the substrate and a biotinylated receptor may bind to the streptavidin.

Figure 3:
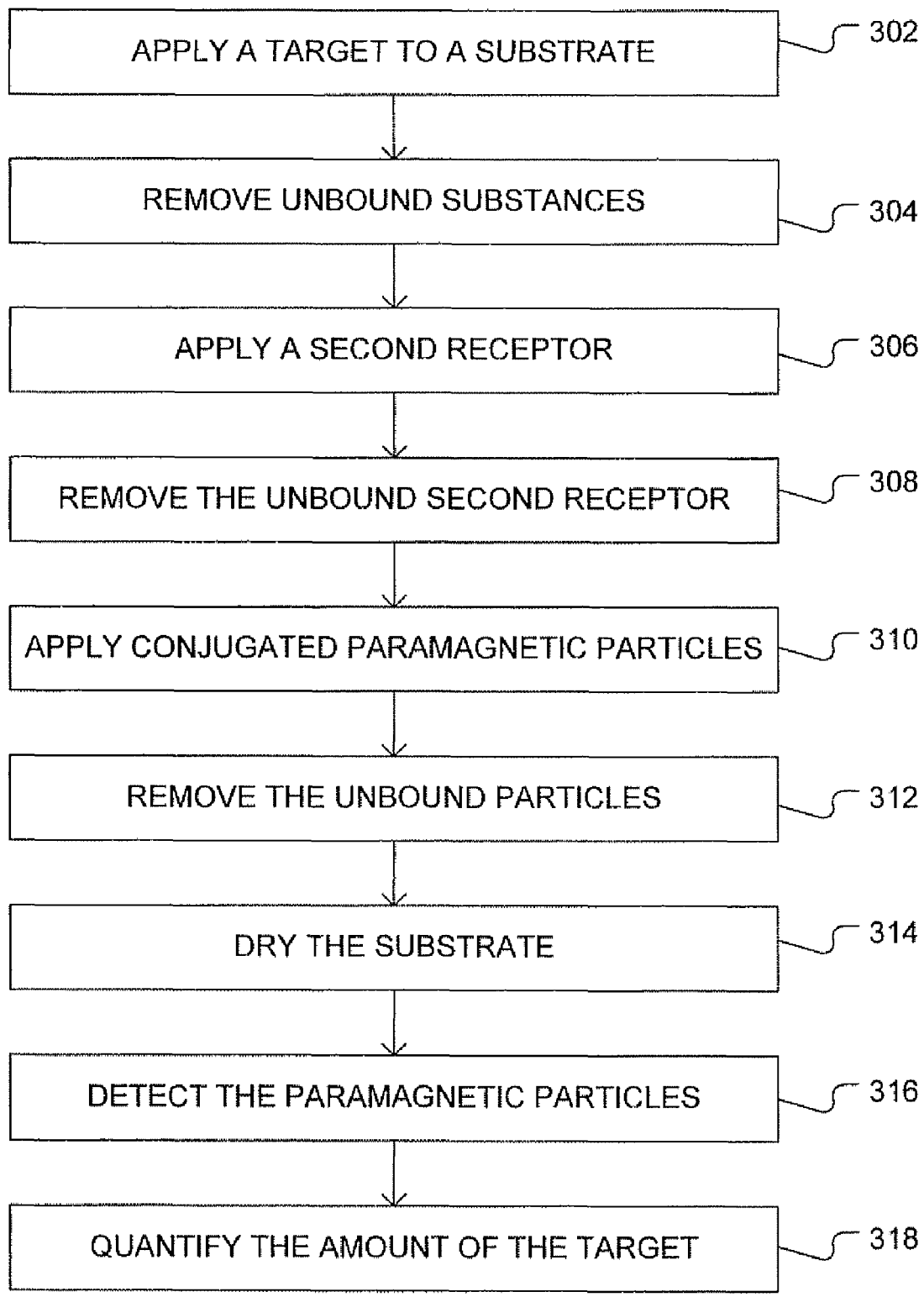
FIGS. 3 and 4 include flow diagrams illustrating methods of detecting target analytes using conjugated paramagnetic particles.

FIG. 3 is a flow diagram illustrating a method of detecting a target analyte using conjugated paramagnetic particles. In an exemplary embodiment, a target analyte or a solution suspected of including the target analyte is applied to or contacted with a substrate, as illustrated at 302. The substrate may include a receptor bound to the substrate. The receptor, for example, may be responsive to the target analyte. In particular, the receptor may specifically bind to the target analyte. In an exemplary embodiment, the substrate is a well of a multi-well plate.

In an exemplary embodiment, unbound substances are removed from the substrate, as illustrated at 304. For example, the unbound substances may be removed from the substrate by rinsing the substrate. In an example, the substrate may be rinsed with water, an aqueous solution, a solvent, or any combination thereof.

A second receptor, such as an antibody, may be applied to the substrate, as illustrated at 306. For example, the second receptor may be included in a solution that is contacted with the substrate. The second receptor may bind to the target analyte. Optionally, unbound second receptors may be removed from the substrate, as illustrated at 308. In an exemplary embodiment, the unbound antibody may be removed by rinsing the substrate. For example, the substrate may be rinsed with water, an aqueous solution, a solvent, or any combination thereof.

In an exemplary embodiment, conjugated paramagnetic particles may be applied to the substrate, as illustrated at 310. For example, the conjugated paramagnetic particles may be included in a solution that is contacted with the substrate. The conjugated paramagnetic particles may bind the second receptor. In an exemplary embodiment, the second receptor is conjugated to biotin and the conjugated paramagnetic particle is an anti-biotin conjugated paramagnetic particle. Further, the anti-biotin conjugated paramagnetic particle may be an anti-biotin antibody conjugated paramagnetic particle.

Unbound conjugated paramagnetic particles may be removed from the substrate, as illustrated at 312. For example, the unbound conjugated paramagnetic particles may be removed by rinsing the substrate, such as with water, an aqueous solution, a solvent, or any combination thereof. Bound conjugated paramagnetic particles may remain in proximity to the substrate.

While applying the target analyte to the substrate, applying the second receptor to the substrate, and applying the conjugated paramagnetic particles to the substrate are illustrated separately, the target, the second receptor, or the conjugated paramagnetic particle may be applied in combination. For example, the second receptor and the conjugated paramagnetic particles may be applied to the substrate concurrently. In another example, the target analyte, the second receptor, and the conjugated paramagnetic particles may be applied to the substrate concurrently.

Optionally, the substrate may be dried, as illustrated at 314. In an exemplary embodiment, the substrate is dried by exposing the substrate to air for a period of time sufficient to remove excess moisture. In an alternative embodiment, the substrate may be dried under vacuum, and in particular, may be lyophilized.

In an exemplary embodiment, the conjugated paramagnetic particles associated with the substrate are detected, as illustrated at 316. In an example, the amount of the conjugated paramagnetic particles associated with the substrate is determined by an analyte detection system. For example, the conjugated paramagnetic particles may perturb an electromagnetic field, such as a radio frequency (RF) signal. A greater perturbation indicates a greater number of paramagnetic particles in proximity to the substrate.

The target analyte may be quantified, as illustrated at 318. In an exemplary embodiment, the quantification of the antigenic substance is based on the amount of paramagnetic particles associated with the substrate. In particular, the perturbation associated with the presence of paramagnetic particles may be correlated to a quantity or concentration of the target analyte. For example, the paramagnetic particle may cause a change in a phase of an RF signal, a frequency shift in the RF signal, an amplitude attenuation in the RF signal, or a combination thereof.

In a particular example, the target analyte may be a human antigen. In such an example, the substrate may include a receptor that is specific to the human antigen. In addition, a non-specific receptor, such as a non-specific anti-human antibody or mixture of anti-bodies may be used as a second receptor or may be conjugated to the conjugated paramagnetic particle used to detect the presence of the human antigen. Such a method may also be envisioned for antigens of other species.

Figure 4:
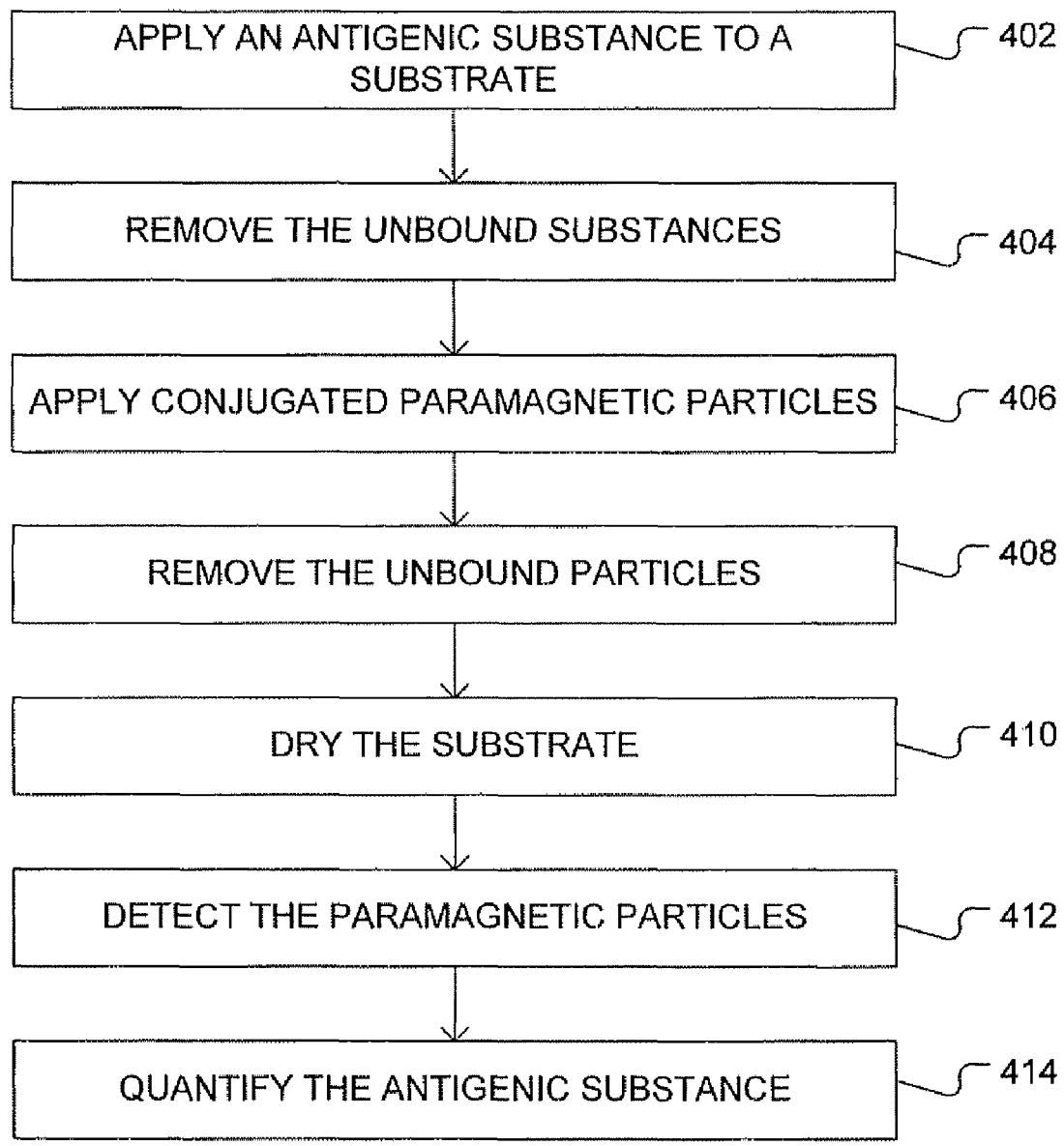

Optionally, the paramagnetic particles may be conjugated to a receptor that is responsive to the target analyte. In such an example, the second receptor is superfluous. In an exemplary embodiment, FIG. 4 includes a flow diagram illustrating a method of detecting an antigenic substance using conjugated paramagnetic particles. In an exemplary embodiment, an antigenic substance is contacted with a substrate, as illustrated at 402. The substrate, for example, may be a well of a multi-well plate. Further, the substrate may include a first antibody attached to the surface of the substrate. The first antibody may be reactive to the antigenic substance.

In an exemplary embodiment, unbound substances are removed from the substrate, as illustrated at 404. For example, the unbound substances may be removed from the substrate by rinsing the substrate.

Conjugated paramagnetic particles may be applied to the substrate, as illustrated at 406. The conjugated paramagnetic particles may be conjugated to a molecule that can bind to the antigenic substance. In an exemplary embodiment, the conjugated paramagnetic particle is conjugated to an antibody reactive to the antigenic substance. Unbound conjugated paramagnetic particles may be removed from the substrate, as illustrated at 408. For example, the unbound conjugated paramagnetic particles may be removed by rinsing the substrate. Optionally, the substrate may be dried, as illustrated at 410. In an exemplary embodiment, the substrate may be dried by exposing the substrate to air for a period of time sufficient to remove excess moisture or may be dried under vacuum.

In an exemplary embodiment, the conjugated paramagnetic particles associated with the substrate are detected, as illustrated at 412. For example, the amount of the conjugated paramagnetic particles associated with the substrate may be determined using an analyte detection system. In particular, the number of paramagnetic particles remaining in proximity to the substrate may influence an electromagnetic field. The number of paramagnetic particles may be correlated with the detected influence on the electromagnetic field.

Based at least in part on the detection of the paramagnetic particles, the presence of antigenic substance may be quantified, as illustrated at 414. For example, a correlation between the amount of antigenic substance and the amount of paramagnetic particles associated with the substrate or the detected influence of the paramagnetic particles on an electromagnetic field may be used to determine the amount of antigenic substance. While the method illustrated in FIG. 4 relates to antigenic substances, the method may also be implemented for other target analytes, and in particular, an ex vivo target analyte.

Figure 5:
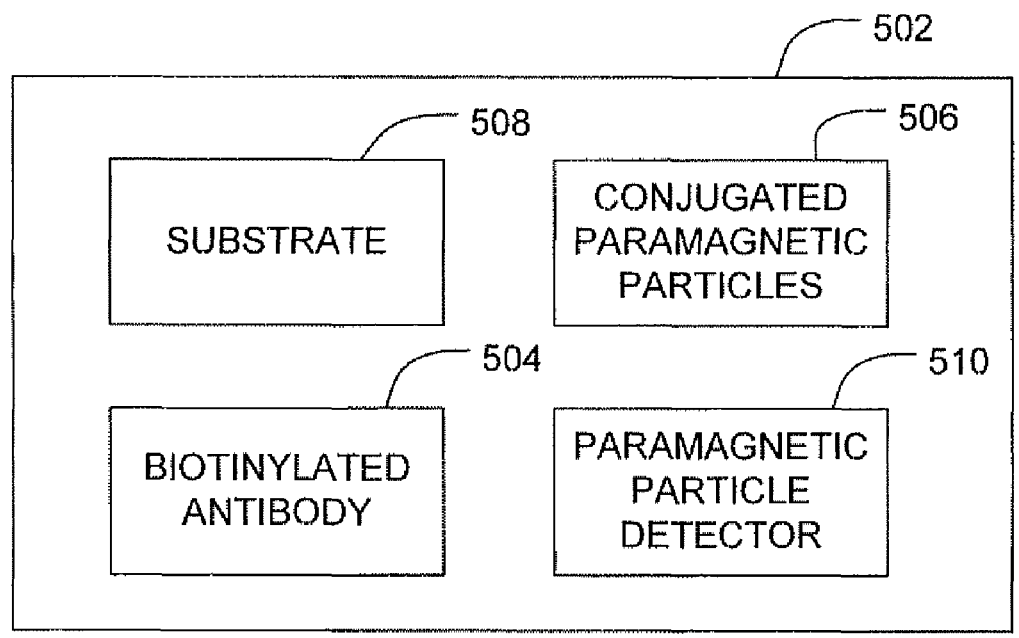
FIGS. 5 and 6 include block diagrams illustrating exemplary detection kits.

To implement the methods described above in relation to FIG. 3 and FIG. 4, a kit may be provided that includes the substrate and the conjugated paramagnetic particles. For example, FIG. 5 includes a block diagram illustrating an exemplary analyte detection kit 502. In an exemplary embodiment, the analyte detection kit 502 includes receptors 504, a conjugated paramagnetic particle 506, a substrate 508, and optionally, a paramagnetic particle detector 510. The substrate 508 may include a receptor bound to the surface of the substrate and reactive or responsive to an intended target analyte. In an exemplary embodiment, the substrate 508 is a multi-well plate. For example, the substrate 508 may include at least 2 wells, such as at least 4 wells. In a particular example, the substrate 508 includes at least 48 wells, such as at least 96 wells, or even, at least 384 wells.

The receptor 504 may be reactive to the intended target analyte. For example, the receptor 504 may bind to the intended target analyte. In addition, the receptor 504 may have characteristic sites that may bind with molecules that are conjugated to the conjugated paramagnetic particles 506. In a particular embodiment, the characteristic site may include biotin and the conjugated paramagnetic particle 506 may be an anti-biotin conjugated paramagnetic particle. In another example, the kit 502 may include another receptor that can bind with the receptor 504 and to which the conjugated paramagnetic particle can bind.

In an exemplary embodiment, the paramagnetic particle 506 is conjugated to a molecule responsive to the receptor 504. For example, the conjugated paramagnetic particle 506 may bind to the receptor 504 when in contact with the receptor 504. In an alternative embodiment, the receptor 504 may be conjugated to the paramagnetic particle 506. The receptor 504 or the conjugated paramagnetic particle 506 may be included in the kit 502 in the form of a lyophilized powder. Alternatively, the receptor 504 or the conjugated paramagnetic particle 506 may be included in the kit 502 as one or more solutions.

The kit 502 optionally may include a paramagnetic particle detector 510. Alternatively, the paramagnetic particle detector 510 may be provided separately. In an exemplary embodiment, the paramagnetic particle detector 510 is configured to determine the amount of conjugated paramagnetic particles 506 associated with the substrate 508. For example, the paramagnetic particle detector 510 may include an antenna or a coil to detect the paramagnetic particle 506. In a particular example, the paramagnetic particle detector 510 may include circuitry configured to determine an influence of the paramagnetic particles on an electromagnetic field and based on the influence, determine a quantity of paramagnetic particles or correlate an amount of the intended target analyte.

Figure 6:
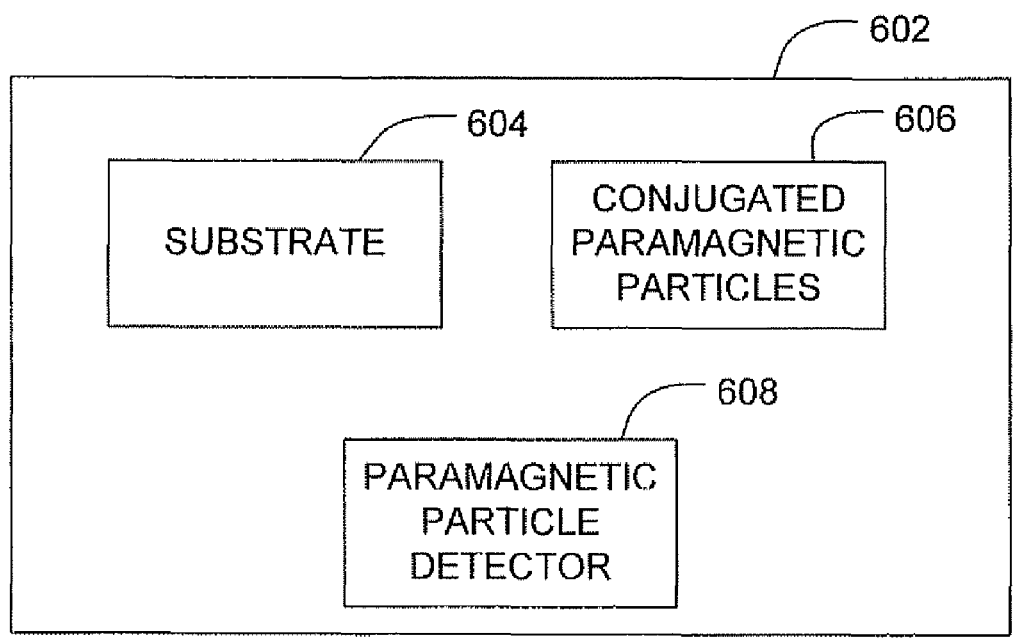

Alternatively, an analyte detection kit may include conjugated paramagnetic particles that bind to an intended target analyte. For example, FIG. 6 is a block diagram illustrating an exemplary analyte detection kit 602. In an exemplary embodiment, the analyte detection kit 602 includes a substrate 604, a conjugated paramagnetic particle 606, and optionally, a paramagnetic particle detector 608. The substrate 604 may include a bound receptor, such as an antibody, reactive to the target analyte. In an example, the substrate 604 is a multi-well plate.

In an exemplary embodiment, the conjugated paramagnetic particle 606 may be reactive to the target analyte. For example, the conjugated paramagnetic particle 606 may be conjugated to an antibody reactive to the analyte. In an exemplary embodiment, the paramagnetic particle detector 608 is configured to determine the amount of conjugated paramagnetic particles 606 that are associated with the substrate. Alternatively, the paramagnetic particle detector 608 may be provided separately.

Figure 11:
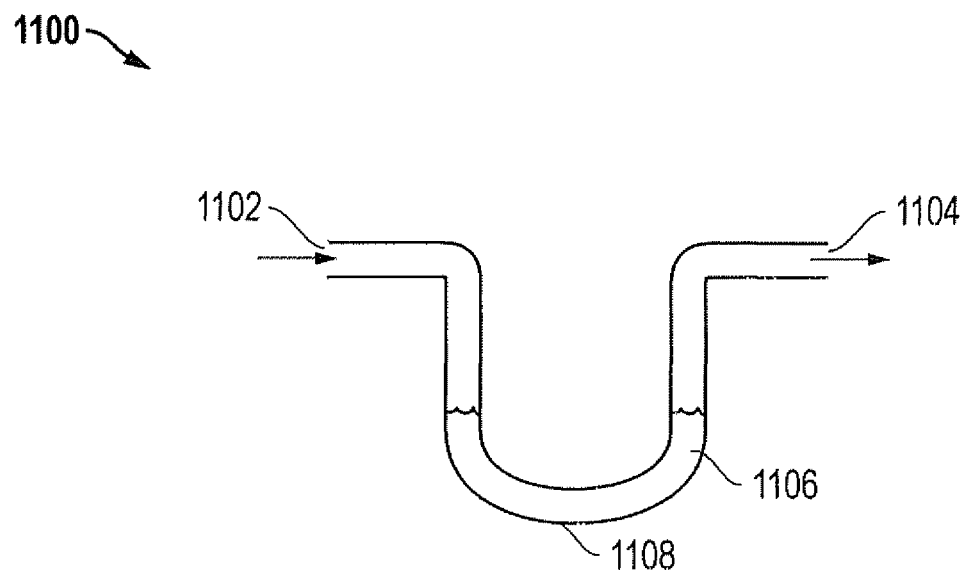
FIGS. 11 and 12 include diagrams illustrating exemplary atmospheric sampling devices.

In addition, a kit may include a sampling mechanism. For example, the kit may include a dropper, a vial, a spoon, tweezers, or any combination thereof. In another exemplary embodiment, the kit may include an atmospheric sampler to acquire samples from air. For example, FIG. 11 and FIG. 12 include illustrations of exemplary atmospheric samplers 1100 and 1200, respectively. In an example, the atmospheric sampler 1100 may include an inlet 1102, a trap 1108, and an outlet 1104. In an embodiment, air may be blown into the inlet 1102 and through the trap 1108. In another embodiment, air may be vacuumed through the outlet 1104, drawing air through the inlet 1102 and the trap 1108. In a particular example, the trap 1108 may include a liquid solution 1106 to trap a target analyte. For example, the trap 1108 may include water, a saline solution, a solvent, or any combination thereof. In a further example, the solution 1106 may include a receptor or conjugated paramagnetic particles. In another example, the trap 1108 may be configured to expose a surface of a substrate that includes receptors to the solution 1106. For example, the trap 1108 may form the substrate or the substrate may be placed in the trap 1108. Alternatively, liquid samples may be drawn from the trap 1108 and contacted with a substrate.

Figure 12:
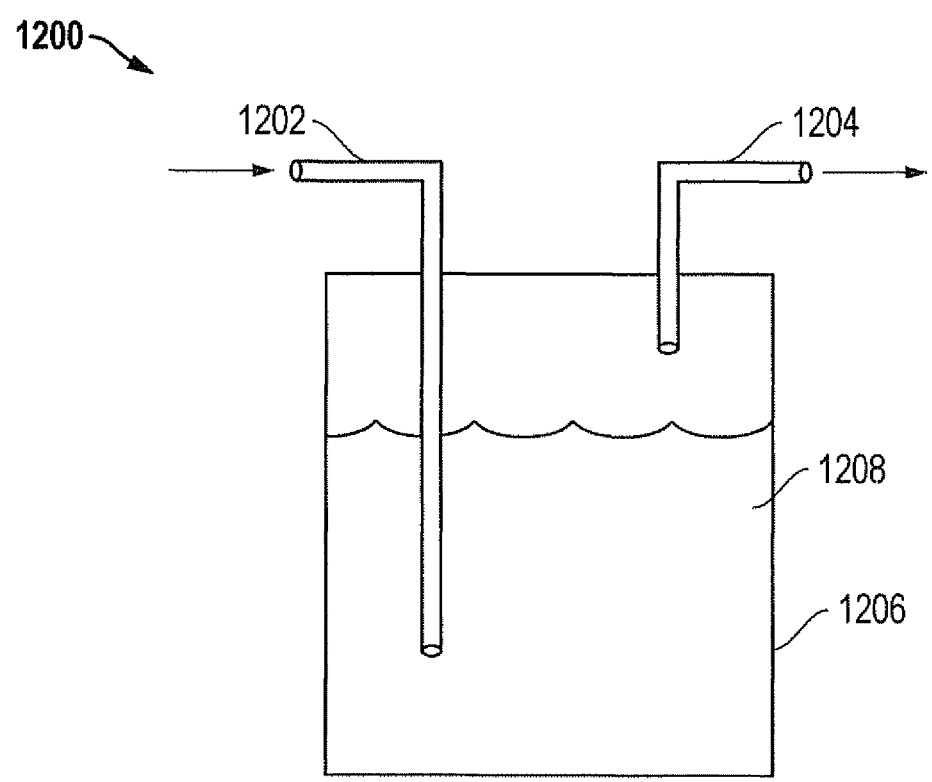

In an alternative example illustrated in FIG. 12, a container or well 1206 may be attached to an inlet tube 1202 and optionally, an outlet 1204. For example, in a closed top system, the container 1206 may be attached to an inlet tube 1202 and to an outlet tube 1204. Atmospheric samples may be blown into the inlet 1202 or vacuumed through the outlet 1204. In an open top system, the container 1206 may be attached to an inlet tub 1202 through which an atmospheric sample is blown. The container 1206 may include a solution 1208 to capture a target analyte. In an additional embodiment, the walls of the container 1206, or in particular, the floor of the container 1206 may have attached receptors that are responsive to the target analyte. In another embodiment, a substrate having attached receptors may be placed in the container 1206. In a further exemplary embodiment, the sample collected in an atmospheric sampler, such as the samplers 1100 or 1200, may be transferred to a well or applied to a substrate.

Figure 7:
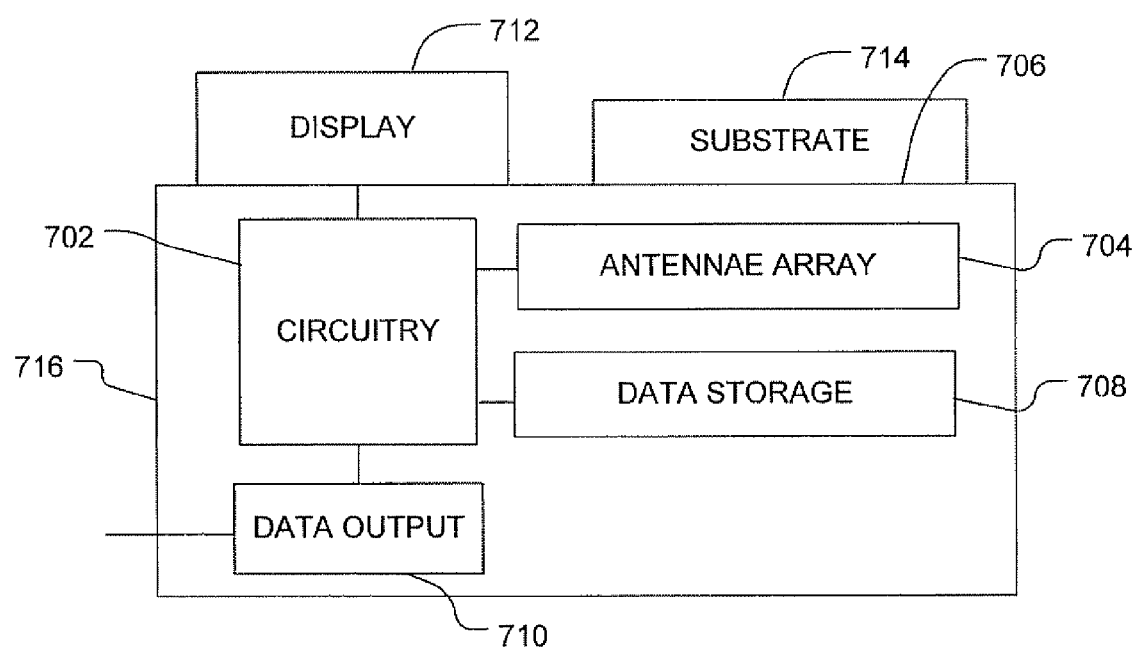
FIG. 7 includes a block diagram illustrating an analyte detection system.

FIG. 7 includes a block diagram illustrating an exemplary analyte detection system 700. In an exemplary embodiment, the analyte detection system 700 includes a circuitry 702, an antennae array 704, and a substrate receiving area 706. The analyte detection system 700 also may include a data storage 708, a data output 710, or a display 712. In a particular example, the circuitry 702, the antennae array 704, the data output 710, and the data storage 708 are included in a housing 716. Alternatively, one or more of the circuitry 702, the antennae array 704, the data output 710 or the data storage 708 are included in one or more housings.

The substrate receiving area 706 may be configured to receive a substrate 714 and place the substrate 714 in proximity to the antenna array 704. For example, the substrate receiving area 706 may be configured to receive a multi-well plate. In particular, the substrate receiving area 706 may be configured to align a multi-well plate with the antennae array 704. For example, the antennae array 704 may include more than one antennae, coils, or styluses that may be aligned with wells of the multi-well plate.

The antennae array 704 may include more than one antenna that may align with one or more portions of a substrate 714 located in the substrate receiving area 706. The antennae array 704 may be coupled to the circuitry 702. The circuitry 702 may manipulate the antenna array 704 to determine the influence of paramagnetic particles on an electromagnetic field, such as an RF signal. In particular, the circuitry 702 may manipulate each antennae of the antennae array 704 to determine the influence of paramagnetic particle in each of the associated wells of the substrate 714.

In an exemplary embodiment, the circuitry 702 includes a set of components that generate an oscillating electromagnetic signal and compare the generated signal to a signal perturbed by the paramagnetic particles. For example, the circuitry 702 may be formed form a set of resistors, transistors, capacitors, and inductors. In an alternative embodiment, the circuitry 702 may include a digital signal processor (DSP) and a direct digital synthesis (DDS) circuit.

In addition, the paramagnetic particle detector 700 may include data storage 708 connected to the circuitry 702. The circuitry 702, for example, may store data on the data storage 708. In addition, the data storage 708 may include parameters and correlations useful by the circuitry 702 to determine the amount of a target analyte. In an example, the data storage 708 may include a hard drive, a removable magnetic media, a removable optical media, a flash media, a random access media, or any combination thereof.

Further, the paramagnetic particle detector 700 may include a data output port 710 coupled to the circuitry 702 to output data. For example, the data output port 710 may be a USB port, a parallel port, a serial port, a network port, or any combination thereof. In a particular example, the data output port 710 may be configured to transmit data to a remote computational system.

In another exemplary embodiment, the paramagnetic particle detector 700 may include a display 712. For example, the display 712 may be coupled to the circuitry 702. The display 712 may be useful for displaying results of tests, configuring the device to detect, or to provide a status of a detection.

Figure 8:
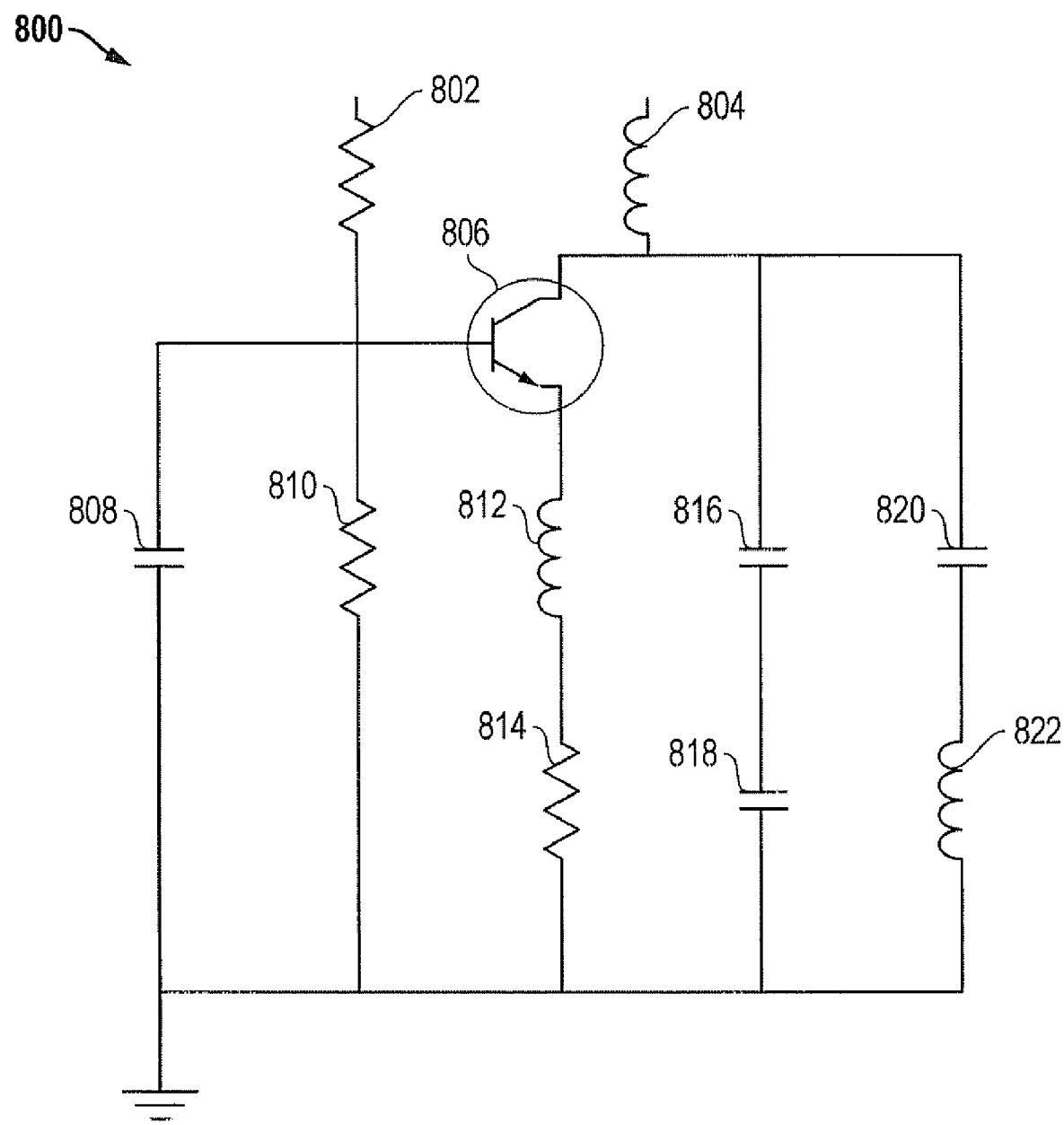
FIGS. 8 and 9 include diagrams illustrating exemplary circuitry for use in an analyte detection system.

FIG. 8 is a diagram illustrating an exemplary circuit 800. In an exemplary embodiment, the circuit 800 includes a transistor 806, three resistors 802, 810, and 814, three inductors 804, 812, and 822, and four capacitors 808, 816, 818, 820.

Figure 9:
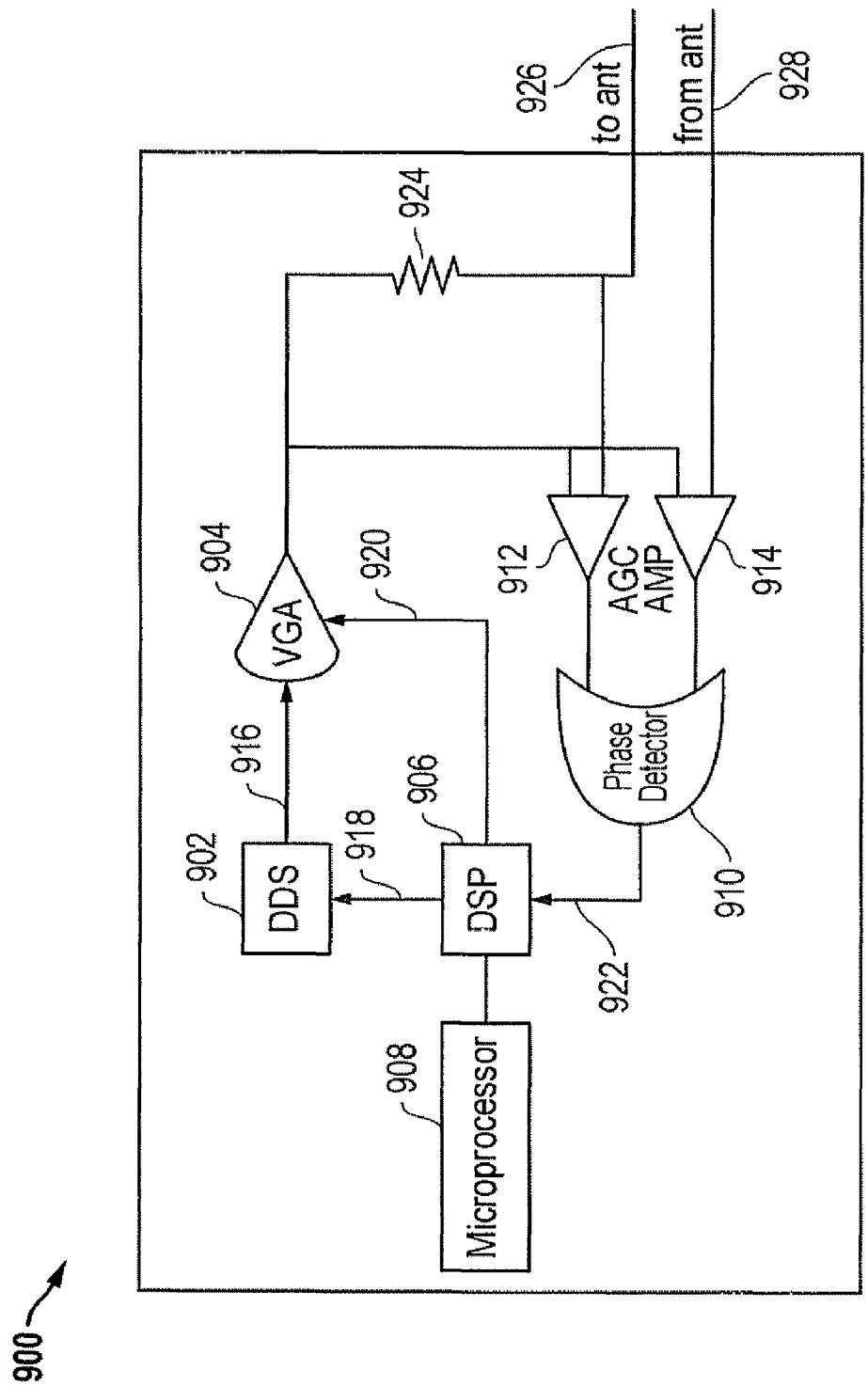

FIG. 9 is a diagram illustrating an exemplary circuitry 900. In an exemplary embodiment, the circuitry 900 includes a direct digital synthesis (DDS) circuitry 902, a variable gain amplifier (VGA) 904, a digital signal processor (DSP) 906, and a phase detector 910. The circuitry 900 may also include two adjustable gain circuits (AGC) 912 and 914 and a resistor 924. In an alternative embodiment, the circuitry 900 may include a microprocessor 908 or may be connected to an external computational system.

In an exemplary embodiment, the circuitry 900 is configured to determine the amount of conjugated paramagnetic particles by measuring a phase shift in a radio frequency (RF) signal. The circuitry 900 may be configured to measure the phase shift by seeking lock points at higher modulation frequencies. For example, the DSP 906 may signal, at 918, the DDS circuit 902 to generate a radio frequency (RF) excitation signal 916 that is transmitted to the VGA 904. The DSP 906 may also adjust the gain, at 920, of the VGA 904. The VGA 904 and the AGCs 912 and 914 may be configured to provide input signals to other components. In particular, the VGA 904 may be connected to the sensor or coil, at 926, via a resistor 924 and may be connected to the AGCs 912 and 914.

The AGCs 912 and 914 may be coupled to the phase detector 910. For example, the AGC 912 may receive input from the VGA 904 and from the output to the antennae 926. In addition, the AGC 914 may receive input from the VGA 904 and input received from the antenna, at 928. The phase detector 910 may receive the output signals from the AGCs 912 and 914 and may provide a phase change output 922 to the DSP 906.

The DSP 906 may be configured to acquire and process phase change data. For example, the DSP 906 may be configured with software to initiate RF signals via the DDS 902 and the VGA 904 and may be configured with software to process the phase change data 922 received from the phase detector 910. In addition, the DSP 906 may include an output to communicate the acquired and processed data, such as to a display, a data storage, another computational system, or any combination thereof. In particular, the DSP 906 may be configured to determine an amount of a target analyte based on a correlation. In another embodiment, the DSP 906 may be further controlled by a microprocessor 908.

In a further embodiment, the circuitry 900 may be coupled to an array of antennae. As such, the circuitry 900 may include a multiplexer controlled by the DSP or another processor to switch between antenna of the array. In another example, a circuit 900 may be provided for each antenna of the array.

Particular embodiments of the above circuitries advantageously have low signal to noise ratios and show limited interference between antennae in close proximity in an array. As such, these particular embodiments permit separate testing of more than one location on a substrate and thus, are useful in performing multiple tests in adjacent wells of a multi-well plate.

Figure 10:
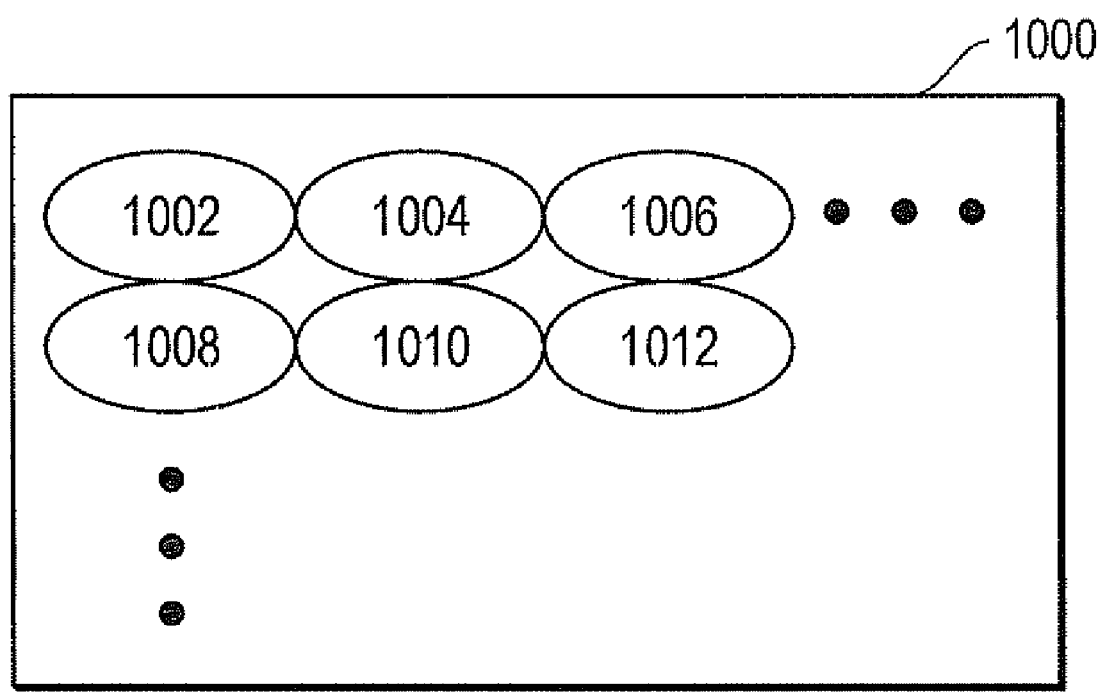
FIG. 10 includes a diagram illustrating an exemplary arrangement of an array of antennae.

In a particular embodiment, the array of antenna is configured to measure paramagnetic particle in an array of locations on a substrate. For example, the substrate may be a multi-well plate. In particular, the array may include at least four antenna in an arrangement wherein at least one antenna of the at least four antenna is adjacent to at least three other antenna of the at least four antenna. For example, FIG. 10 is a diagram illustrating an exemplary arrangement 1000. The arrangement may include at least 4 positions. As illustrated, the arrangement 1000 includes at least 6 positions 1002, 1004, 1006, 1008, 1010, and 1012. As illustrated, there may be additional positions extending the arrangement of rows and columns. In a particular example, the rows and columns extend in a ratio of two rows to three columns. For example, the array may include at least about 48 positions. In another example, the array may include at least about 96 positions. In a further example, the array may include at least about 384 positions, such as at least about 1536 positions.

Further, any two adjacent positions may have center points that are not greater than 2 cm apart. For example, two positions may have center points that are not greater than 1.5 cm apart.

In an exemplary embodiment, the position 1002 is adjacent three other positions 1004, 1008, and 1010 and the position 1004 is adjacent to the other positions, 1002, 1006, 1008, 1010, and 1012. In a further example, the position 1010 may be adjacent to at least 5 other positions, such as 8 positions.

In an exemplary embodiment, the arrangement may align with the arrangement of at least a portion of positions of a substrate. For example, the array may be configured to align the antennae with a set of wells in a multi-well substrate. In a particular example, the substrate may include at least four wells in an arrangement wherein at least one well of the at least four wells is adjacent to at least three other wells of the at least four wells. As such, the positions illustrated in FIG. 10 may correspond to positions on a substrate. In particular, there may be additional wells extending the arrangement of rows and columns. For example, the rows and columns may extend in a ratio of two rows to three columns. In a particular example, the substrate may include at least about 48 wells. In another example, the substrate may include at least about 96 wells. In a further example, the substrate may include at least about 384 wells, such as at least about 1536 wells. Further, any two adjacent wells may have center points that are not greater than 2 cm apart, such as not greater than 1.5 cm apart.

EXAMPLES

Example 1

Procedure for Coating a 96-Well Plate with an Antibody

One can either use Costar ELISA plates or Immulon II plates, both of which are available from VWR.

Dilute the 5× Coating Buffer 1 (CB1, Immunochemistry Technologies LLC (ICT)) by adding 1 part buffer to 4 parts deionized water (100 mL CB1 to 400 mL diH2O, yielding a total volume of 500 mL) and mix for 15 minutes. Dilute antibody into the Coating Buffer 1. The final concentration of antibody is 5 ug/ml. Let the solution stir (10-15 minutes) and pipette onto the plate (coating volume generally ranges between 50-300 mL per well).

Once added to the plate, incubate the coating solution from 3-24 hours at room temperature protected from light (minimize evaporation by individually covering each plate with a plate sealer, wrapping a stack in plastic wrap, or placing plates in a humidified storage box, and cover). After incubation, dump or aspirate the coating solution out of the wells. Wash the plate 2-4 times with ICT's wash buffer. Aspirate and pipette one of ICT's block buffers onto the plate at a higher volume than the coating solution (300-400 uL per well).

Once added to the plate, incubate the block buffer from 3-24 hours at room temperature protected from light (minimize evaporation by individually covering each plate with a plate sealer, wrapping a stack in plastic wrap, or placing plates in a humidified storage box, and cover). Aspirate the block buffer. The assay can be run at this point, or the plate can be dried and packaged for later use.

Dry the plate by letting it sit on the bench top from 2-24 hours (but protected from light—loosely cover with aluminum foil), or dry in a drying oven from 2-24 hours at room temperature or warmer. When dry, seal the plate in an air-tight foil pouch with a desiccant and store at RT or 2°-8° C. protected from light.

Example 2

Conjugating a Paramagnetic Bead to an Antibody

Washing Procedure

Resuspend Dynabeads M-280 Tosyl-activated thoroughly by pipetting or vortexing for approximately 1 min. Avoid foaming. Immediately pipette the volume of beads to be used into the desired test tube. Place the tube on a magnet (Dynal MPC) for 2 minutes or until the beads have migrated to the side of the tube and the liquid is clear.

Pipette off the supernatant carefully, leaving beads undisturbed. Remove the test tube from the magnet and re-suspend the beads carefully in an ample volume of Buffer B (See Below). Mix gently for 2 min. After applying the magnet and pipetting off the supernatant, re-suspend the washed beads in the same volume of Buffer B as taken from the tube in step 4 above or to the desired concentration. The M-280 Tosyl-activated Dynabeads are now washed and ready for coating.

Coating Procedure to Add PMP to Antibody

Make a homogeneous suspension of the Dynabeads M-280 Tosyl-activated by using a pipette and by vortexing for approximately 1 min. Pipette out the desired number of beads and wash as described above. Dissolve the antibody in Buffer B. Use 107 beads per 3 mg of antibody. Re-suspend the Dynabeads thoroughly (remove tube from the magnet and vortex or use ultrasound). Add antibody and continue to vortex for 1 minute.

Incubate for 16-24 h at 37° C. with slow tilt rotation. Lower temperature may be used for temperature sensitive antibodies/proteins. Longer incubation times can be used to ensure covalent binding. After incubation, place the tube on the magnet for 2 minutes, or until the beads have migrated to the side of the tube, and remove the supernatant. Generally, 30-80% of the added antibody will bind to the Tosyl-activated paramagnetic beads. Increasing the incubation time increases the yield.

Wash the coated beads four times as follows:
2× in Buffer C for 5 minutes at +4° C.
1× in Buffer D for 24 h at +20° C. or for 4 h at 37° C.
1× in Buffer C for 5 minutes at +4° C.

The Dynabeads M-280 Tosyl-activated are now coated with antibody and are ready for use. Store the Dynabeads that have been coated with antibody in Buffer C at a known concentration. The coated beads can usually be stored for several months at +4° C., depending on the stability of Antibody. 0.02% sodium azide may be added as a bacteriostatic agent.

Buffer A: 0.1 M Na-phosphate buffer pH 7.4: 2.62 g Na H2PO4 (MW 137.99) 14.42 g Na2HPO4 (MW 177.99). Dissolve in distilled water. Adjust to 1000 ml.

Buffer B: 0.1 M borate buffer pH 9.5: 6.183 g $H_3BO_3$ (MW 61.83). Dissolve in 800 ml distilled water. Adjust pH to 9.5 using 5 M NaOH and adjust volume to 1000 ml with distilled water.

Buffer C: PBS pH 7.4 (phosphate buffered saline) with 0.1% (w/v) BSA: Add 0.88 g NaCl (MW 58.4) and 0.1% (w/v) BSA to 80 ml 0.01 M Na-phosphate pH 7.4. Mix thoroughly and adjust volume to 100 ml with 0.01 M Na-phosphate pH 7.4.

Storage & Stability

When stored in unopened vials at 4° C., Dynabeads M-280 Tosyl-activated are stable for up to one year. Antibody-coated Dynabeads M-280 Tosyl-activated stored for more than two weeks should be washed once for 5 min in PBS/BSA before use.

Example 3

The lyophilized standard IL-15 (Biosource IL-15 kit, Cat. No. KHC0152/KHC0151) is reconstituted at a concentration of 10,000 pg/ml in 1.12 ml of 50% standard diluent (Biosource IL-15 kit, Cat. No. KHC0152/KHC0151) and 50% serum (normal human female pooled—Bioreclamation), Cat. No. HMSRM-F) and a serial dilution is performed in 50% diluent and 50% serum, so that 2 standard curves are established, each including the following points (0 pg/ml, 9.75 pg/ml, 39 pg/ml, 156 pg/ml, 312 pg/ml, 625 pg/ml, 1250 pg/ml and 2500 pg/ml). The data for the two standard curves are combined to make a single standard curve. In all cases an offset value, that results from the fact that plastic is slightly magnetized in an electric field (Enpuku et al., 1999), is obtained by measuring 10 empty wells, averaging them, and subtracting that value from all other measurements. The experimental points are established by diluting 50 ul of the samples in an equal volume of standard diluent.

Add 100 ul of biotinylated, anti-IL-15 (Biotin Conjugate Biosource IL-15 kit, Cat. No. KHC0152/KHC0151) to each well. Tap the plate gently to mix and then cover and allow to incubate for 1 hour at room temperature.

Decant wells and wash them 4 times with Wash Buffer (Biosource IL-15 kit, Cat. No. KHC0152/KHC0151), using a strong stream from a squirt bottle and washing for 30 seconds each.

Dilute Miltenyi Biotech Anti-Biotin MACSIBeads (Miltenyi Biotech, Cat. No. 130-091-147) paramagnetic beads 10-fold in Streptavidin-Horse Radish Peroxidase Diluent (Biosource IL-15 kit, Cat. No. KHC0152/KHC0151). Continuously swirl diluted magnetic beads as they have a tendency to fall out of solution. Add 100 ul of the diluted magnetic beads to each well. Tap plate gently to mix, cover and allow to incubate for 1 hour at room temperature.

Decant wells and wash them 4 times with Wash Buffer (Biosource IL-15 kit, Cat. No. KHC0152/KHC0151), using a strong stream from a squirt bottle, for 30 seconds each. Tap plate dry by tapping it upside down smartly on a pillow of absorbent paper.

Let plate dry and measure all points, including 10 empty wells to establish the offset to be subtracted from all measurements.

Example 4

Antibodies may be biotinylated in accordance with the methods outlined in:

Measurement of Polyclonal Immunoglobulin Synthesis Using ELISA Support Protocol: Biotinylation of Immunoglobulin, Thomas B. Nutman, National Institute of Allergy and Infectious Diseases, Bethesda, Md., John E. Coligan, Ada M. Kiruisbeek, David H. Margulies, Ethan M. Shevach, and Warren Strober (eds.), Current Protocols in Immunology Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of detecting an endogenous human target, the method comprising:
    applying the endogenous human target to a substrate, the substrate having a first receptor attached to the substrate, the first receptor specific to the endogenous human target;
    applying non-specific anti-human antibodies conjugated to paramagnetic particles to the substrate, the non-specific anti-human antibodies binding to the endogenous human target;
    washing the substrate; and
    detecting the paramagnetic particles to detect the endogenous human target.

2. The method of claim 1, wherein the first receptor is specific to the endogenous human target.

3. A method of detecting an endogenous human target, the method comprising:
    applying the endogenous human target to a substrate, the substrate having a first receptor attached to the substrate, the first receptor specific to the endogenous human target;
    applying non-specific anti-human antibodies to the substrate, the non-specific anti-human antibodies binding to the endogenous human target;
    applying conjugated paramagnetic particles to the substrate, the conjugated paramagnetic particles adapted to respond to the non-specific anti-human antibody;
    washing the substrate; and
    detecting the paramagnetic particles to detect the endogenous human target.

4. The method of claim 3, wherein the non-specific anti-human antibodies are conjugated to a streptavidin group.

5. The method of claim 4, wherein the conjugated paramagnetic particles are biotinylated.

6. The method of claim 4, wherein the conjugated paramagnetic particles are conjugated to an anti-streptavidin antibody.

7. The method of claim 3, wherein the first receptor is an antibody specific to the human target.

8. The method of claim 3, wherein the endogenous human target is a protein.

9. The method of claim 3, wherein the endogenous human target is a metabolite.

10. The method of claim 3, wherein detecting the paramagnetic particles includes detecting the influence of the paramagnetic particles on an electromagnetic field.

11. The method of claim 10, further comprising determining an amount of the endogenous human target based on a correlation to the influence of the paramagnetic particles on the electromagnetic field.

12. The method of claim 1, wherein the endogenous human target is a protein.

13. The method of claim 1, wherein the endogenous human target is a metabolite.

14. The method of claim 13, wherein the metabolite is a metabolite of a disease.

15. The method of claim 1, wherein detecting the paramagnetic particles includes detecting the influence of the paramagnetic particles on an electromagnetic field.

16. The method of claim 15, further comprising determining an amount of the endogenous human target based on a correlation of the influence of the paramagnetic particles on the electromagnetic field.

17. A method of detecting an endogenous human target, the method comprising:
    applying the endogenous human target to a substrate, the substrate including an immobilized antibody specific to the endogenous human target, the endogenous human target binding to the immobilized antibody;
    applying paramagnetic particles conjugated to non-specific anti-human antibodies, the non-specific anti-human antibodies binding to the endogenous human target, whereby the paramagnetic particles are immobilized relative to the substrate washing the substrate;
    applying an electromagnetic field across the substrate, the paramagnetic particles having an influence on the electromagnetic field; and
    determining the amount of the endogenous human target based on a correlation associated with the influence of the paramagnetic particles on the electromagnetic field.

18. The method of claim 17, wherein the endogenous human target is a metabolite.

19. The method of claim 18, wherein the metabolite is a metabolite of a disease.

20. The method of claim 17, wherein the endogenous human target is a protein.

* * * * *